US00PP10807P

United States Patent [19]

Osiecki

[11] Patent Number: Plant 10,807

[45] Date of Patent: Feb. 23, 1999

[54] SPATHIPHYLLUM PLANT NAMED 'S17'

[75] Inventor: Marian W. Osiecki, Marianna, Fla.

[73] Assignee: Oglesby Plants International, Inc., Altha, Fla.

[21] Appl. No.: 992,532

[22] Filed: Dec. 17, 1997

[51] Int. Cl.[6] ..... A01H 5/00

[52] U.S. Cl. ..... Plt./88.1

[58] Field of Search ..... Plt./88.1

*Primary Examiner*—Elizabeth Kemmerer

*Attorney, Agent, or Firm*—Rothwell, Figg, Ernst & Kurz

[57] ABSTRACT

A new and distinct cultivar of Spathiphyllum is provided. The plant is large, full, symmetrical, suitable for production in a 15–25 cm pot from a single tissue culture produced microcutting; grows vigorously; branches freely; has abundant natural flowering; has large, glossy leaves; straight, thick, strong peduncles, large, bright white spathes with very little green coloration. The first inflorescence is exceptionally large and of a superior quality.

2 Drawing Sheets

SUMMARY OF THE INVENTION

This invention relates to a new and distinct Spathiphyllum cultivar characterized by the following combination of repeatedly observed traits:

1. Large size;
2. full growth habit;
3. vigorous growth;
4. abundant branching;
5. abundant natural flowering;
6. large, glossy leaves;
7. straight, thick, strong peduncles;
8. large, bright white spathes with very little green coloration;
9. first inflorescence exceptionally large and of superior quality;

and primarily selected for those characteristics being so selected from the progeny of the cross stated below in a cultivated area near Altha, Fla.

ORIGIN AND ASEXUAL REPRODUCTION

The new cultivar is a product of a planned breeding program carried out at Oglesby Plants International Inc. near Altha, Fla. The female parent was a selected clone of Spathiphyllum 'Viscount' and the male parent was a selected clone of Spathiphyllum 'Supreme'. The cross was made in 1991, the plant was selected in 1993 and has since been reproduced by tissue culture in the vicinity of Altha, Fla. with the characteristics stated, found to be maintained through successive generations.

This new cultivar has been identified as Spathiphyllum 'S17'. It is possible that other identification will be adopted in the trade, but the name selected will serve for the purposes hereof.

BRIEF DESCRIPTION OF THE PHOTOGRAPHS

The accompanying photographs show as nearly true as it is reasonably possible, in a color illustration of this character, typical specimens of the plant parts of the new cultivar. The plant of 'S17' was approximately 23 months from planting a single tissue culture produced microcutting and was grown in a 25 cm pot.

In the photographs:

DETAILED DESCRIPTION OF THE NEW CULTIVAR

Figure 1:
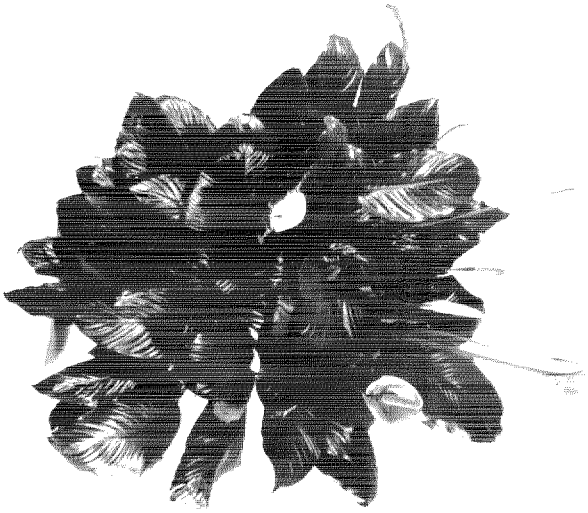
FIG. 1 depicts the whole plant.
Figure 2:
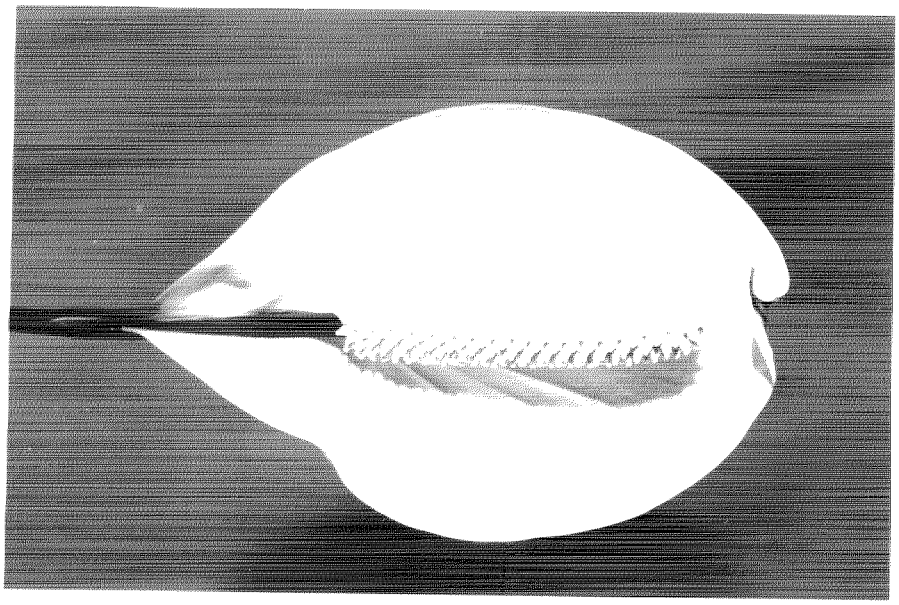
FIG. 2 illustrates the mature inflorescence.
Figure 3:
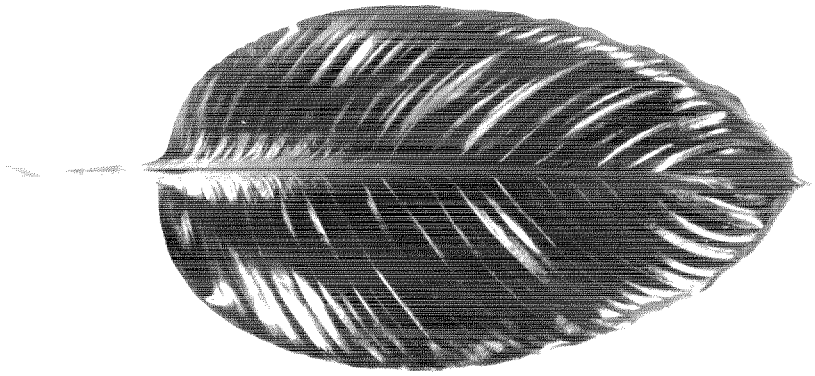
FIG. 3 illustrates the top of a mature leaf.
Figure 4:
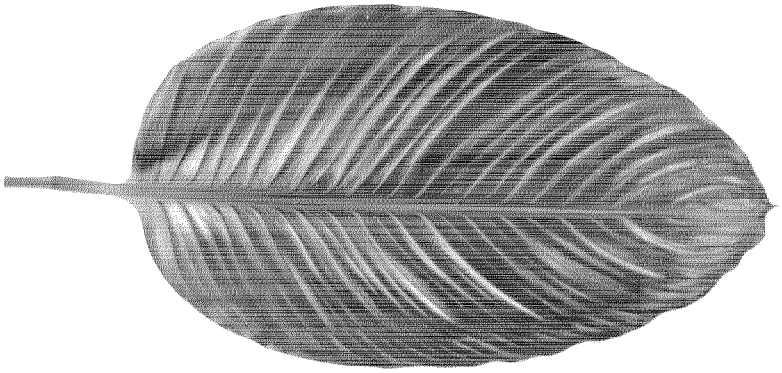
FIG. 4 illustrates the bottom of a mature leaf.

The following observations and measurements describe plants grown near Altha, Fla. under greenhouse conditions. These observations and measurements were recorded in April and May, 1996 from mature plants (about 23 months from planting tissue cultured microcuttings) grown in 25 cm pots. Fully developed organs on main stems were used for measurements. Color values were determined on May 1, 1996 under a natural, indirect light of approximately 350–430 foot-candles. Color references are made to The R.H.S. Colour Chart, except where general color terms of ordinary significance are used.

'S17' has not been observed under all possible environmental conditions. The phenotype may vary with variations in environment and horticultural practices, such as temperature, light intensity, day length, fertilization, propagation method, etc., without any change in genotype.

Parentage:

*Female parent.*—selected clone of Spathiphyllum 'Viscount'.

*Male parent.*—selected clone of Spathiphyllum 'Supreme'.

Propagation: Plant tissue culture.

Plant:

*Growth habit.*—Large, full, symmetrical, well branched, with distinct main stem.

*Height.*—Foliage 69–77 cm, with spathes 102–118 cm.

*Width.*—122–132 cm.

The following description of leaves and inflorescences are based on organs produced on a main stem in each 25 cm pot. Only the first inflorescence and the two leaves preceding it were analyzed; leaves and inflorescences of this general type determine the character of the plant. Leaf blades of many leaves on side shoots and many leaves produced on main stems after the first inflorescence are smaller, substantially narrower, flatter and have more cuneate base.

Petiole:

*Length.*—Leaf supporting inflorescence: 38.0–48.5 cm. Leaf penultimate to leaf supporting inflorescence: 33.0–41.0 cm.

*Diameter (immediately below geniculum).*—7.5–9.0 mm.

*Geniculum.*—2.5–4.3 cm long, 9.1–10.1 mm in diameter.

Leaf Blade:

*Shape.*—Elliptic to ovate; width divided slightly unequally by midrib; tip — acuminate with cuspidate tendencies, slightly curved; base — obtuse, narrowly decurrent on peduncle; margin slightly wavy; often each lobe slightly convex.

*Size.*—Leaf supporting inflorescence: 36.0–41.5 cm long by 21.2–23.0 cm wide; length to width ratio 1.7–1.9:1. Leaf penultimate to leaf supporting inflorescence: 37.0–42.2 cm long by 19.8–21.7 cm wide; length to width ratio 1.8–2.1:1.

*Texture.*—Smooth, glossy; young leaves highly polished.

*Veins.*—Well defined and sunken in the adaxial leaf surface.

*Color.*—Mature leaf: Adaxial: darker than 147A (yellow-green). Abaxial: between 147A and 147B (yellow-green). Young fully unrolled leaf: Adaxial: similar to, but a little more yellow than 137A-B (green). Abaxial: 137C (green).

Inflorescence:

*Arrangement.*—Spathes carried on straight, strong, thick peduncles a moderate distance from the foliage. Spathe length to spadix length ratio 1.4–1.9:1. First spathe on a main stem exceptionally large and carried on very thick peduncle; subsequent inflorescences usually have slightly smaller spathes and slightly thinner peduncles; young side shoots occasionally produce much smaller inflorescences. At inflorescence maturity spadix and spathe edges (except for the distal portion) are almost in the same plane with peduncle or they slightly lean forward; they retain a near vertical position through senescence; very rarely do spathes lean backward.

Peduncle:

*Size.*—82.5–96.5 cm long; 9.6–11.7 mm in diameter immediately below spathe; 2–3 cm long section immediately below spathe is approximately 1.0–1.5 mm thicker than the lower portion; peduncle occasionally bends at the transition zone.

*Color (immediately below spathe).*—Front: 147B (yellow-green) with some addition of 137A-B (green). Back: similar to 147B (yellow-green).

*Stipe.*—0.7–0.9 cm long, 9.1–10.0 mm in diameter.

Spathe:

*Shape.*—Elliptic with some ovate tendencies, cupped through senescence; tip — acuminate, twisted; base cuneate, variably asymmetric.

*Size.*—23.0–26.4 cm long by 13.0–14.9 cm wide; length to width ratio 1.5–2.0:1.

*Color.*—155B, D (white); green coloration on back side is limited to midrib and tip; at the base of the stipe midrib is 146A-B with some 147B (all yellow-green). Narrow midrib in the distal part is 144A or 146B-C except for the tip, where it becomes a little darker-146A (all yellow-green); a diffused 146B-C is present on both sides of midrib in the tip. Front side of the tip has small amount of green coloration similar to that on the back side. Short distal section of midrib on the front side is green too.

Spadix:

*Size.*—14.3–16.0 cm long; 1.4–1.9 cm in diameter.

*Color.*—Similar to 158A (yellow-white).

Botanical flower:

*Perianth.*—Visible between pistils, segments united.

*Pistil.*—Acute, stigma prominent

*Stamens.*—Not visible before pollen release.

Flowering: Flowers naturally in 15 cm pots, approximately 14–15 months from planting tissue culture produced microcuttings. In a 25 cm pot at approximately 23 months approximately four to seven white spathes present above foliage.

Spathe longevity: Spathe remains white for up to 5 weeks following bud appearance above foliage and then gradually changes to a green color.

Roots: Numerous, thick, fleshy white main roots with yellow root caps, lateral roots not very abundant.

Disease and insect resistance: No unusual susceptibility to diseases or insects noted to date.

Comparison with the Known Cultivars

The new cultivar can be compared to the known cultivars 'Supreme' and 'Lynise'. Observations for comparisons were made on plants grown under similar conditions in a greenhouse near Altha, Fla.

'S17' is distinguished from both cultivars by it's more abundant branching; more symmetrical and fuller growth habit; more abundant natural flowering; shorter petioles; more glossy leaf blades; closer proximity of spathes to foliage; much larger first inflorescence; brighter white color of spathes and less green coloration on spathes.

'S17' further distinguished from 'Lynise' by its darker green, wider and more roundish leaf blades.

'S17' is further distinguished from 'Supreme' by possessing some distinctly wider and more roundish leaf blades.

I claim:

1. A new and distinct cultivar of Spathiphyllum plant named 'S17', substantially as described and illustrated herein, characterized particularly as to novelty by its large size; vigorous growth; abundant branching; abundant natural flowering; spathes of bright white color with limited green coloration; thick, strong, straight peduncles and large spathes on main stem; first inflorescence exceptionally large and of superior quality; large, glossy leaves.

* * * * *